United States Patent
Uchida et al.

(10) Patent No.: US 7,262,836 B2
(45) Date of Patent: Aug. 28, 2007

(54) APPARATUS FOR MEASURING BIOLOGICAL INFORMATION AND METHOD FOR MEASURING BIOLOGICAL INFORMATION

(75) Inventors: Shinji Uchida, Neyagawa (JP); Kiyoko Oshima, Shijonawate (JP); Masahiko Shioi, Katano (JP)

(73) Assignee: Matsushita Electrical Industrial Co., Ltd., Osaka (JP)

( * ) Notice: Subject to any disclaimer, the term of this patent is extended or adjusted under 35 U.S.C. 154(b) by 414 days.

(21) Appl. No.: 10/489,175

(22) PCT Filed: Feb. 17, 2003

(86) PCT No.: PCT/JP03/01677

§ 371 (c)(1),
(2), (4) Date: Mar. 10, 2004

(87) PCT Pub. No.: WO03/071254

PCT Pub. Date: Aug. 28, 2003

(65) Prior Publication Data

US 2004/0242978 A1 Dec. 2, 2004

(30) Foreign Application Priority Data

Feb. 21, 2002 (JP) .............................. 2002-044634
Nov. 27, 2002 (JP) .............................. 2002-344472

(51) Int. Cl.
*G01N 1/00* (2006.01)
(52) U.S. Cl. .......................................... 356/36; 356/38
(58) Field of Classification Search .................. 356/36, 356/38, 244; 600/319, 326, 365, 309, 310
See application file for complete search history.

(56) References Cited

U.S. PATENT DOCUMENTS

| 4,490,618 A | | 12/1984 | Cielo |
| 5,172,182 A | * | 12/1992 | Sting et al. ............... 356/244 |
| 5,965,889 A | | 10/1999 | Brierley |

(Continued)

FOREIGN PATENT DOCUMENTS

CN 1271562 A 11/2000

(Continued)

OTHER PUBLICATIONS

Hideo, Fukushima, et al. "Noninvasive Blood Glucose Measurement." pp. 1-15 (English translation of BME, vol. 5, No. 8 pp. 16-21).

*Primary Examiner*—Roy M. Punnoose
(74) *Attorney, Agent, or Firm*—McDermott Will & Emery LLP (57) ABSTRACT

In order to solve the problem of a prior art biological attribute measuring device, i.e., measurement data is apt to vary because of unstable contact due to difficulty in controlling a thickness of a saliva layer and pain caused during the measurement, is provided a biological attribute measuring device including a contact device having a portion, at least part of which is a curved surface, for abutting against a measuring region to apply light to the measuring region, a light detecting means for detecting at least one selected from the group consisting of transmitted light, reflected light, scattered light and transmitted/reflected light from the measuring region and a measuring means for measuring a specific component in the measuring region based on the detection result.

7 Claims, 5 Drawing Sheets

| U.S. PATENT DOCUMENTS | | | |
|---|---|---|---|
| 6,128,091 A | 10/2000 | Uchida et al. | |
| 6,141,100 A | 10/2000 | Burka et al. | |
| 6,424,849 B1 * | 7/2002 | Berman et al. | 600/316 |

FOREIGN PATENT DOCUMENTS

| GB | 2 329 977 A | 4/1999 |
|---|---|---|
| JP | 9-113439 | 5/1997 |
| JP | 9113439 * | 5/1997 |
| JP | 11-064216 | 3/1999 |
| JP | 11-166889 | 6/1999 |
| JP | 2000-146830 A | 5/2000 |
| WO | WO 96/27784 | 9/1996 |
| WO | WO 99/20996 | 4/1999 |

* cited by examiner

Prior Art

FIG. 5

Prior Art

APPARATUS FOR MEASURING BIOLOGICAL INFORMATION AND METHOD FOR MEASURING BIOLOGICAL INFORMATION

TECHNICAL FIELD

The present invention relates to biological attribute measurement in which biological attribute such as a blood glucose level in a living body is measured noninvasively by making use of transmitted light, reflected light, scattered light or transmitted/reflected light. More specifically, the present invention relates to a method of measuring a concentration of a specific component such as glucose, cholesterol or ethanol and a contact device used in the method.

BACKGROUND ART

Conventionally, there have been proposed various methods of measuring a specific component in a living body or a specimen such as a solution using an attenuated total reflectance (ATR) measurement device.

A patient with advanced diabetes owns an easy-to-use blood glucose determination device of blood-collecting type so that she can adopt a method of determining a blood glucose level by collecting blood by herself. Recently, however, development in noninvasive measurement is in progress. For example, there has been proposed a method of using an ATR (attenuated total reflectance) prism, in which attenuated total reflection of incident light is repeated at an interface between a reflection surface of the prism and a living body, and then light emitted to the outside of the prism is analyzed. Japanese Laid-Open Patent Publication No. HEI 9-113439 (page 3 and FIG. 1) discloses a measuring method by sandwiching an ATR prism in a mouth or between fingers.

Figure 4:
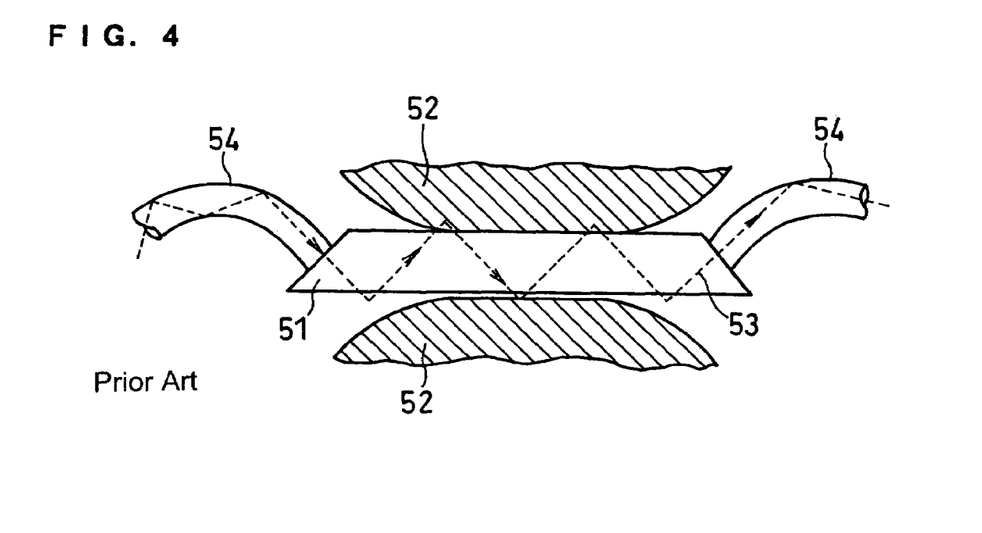
FIG. 4 is a view illustrating the operation of a conventional biological attribute measuring device.

In the method of the above-described publication, evanescent wave (so-called penetrating wave) is applied to a quantitative analysis. As shown in FIG. 4, light 53 propagated through an optical fiber 54 travels in an ATR prism 51 while slightly seeping out, and the seeped light goes into lips 52 and then is reflected. That is, part of the light 53 enters the lips 52 and is affected by components in body fluid existing in the lips 52. For this reason, variations in reflectance and absorptance of the body fluid can be detected by measuring the amount of the reflected light, or returned light. Thereby, information about the components in the body fluid can be obtained.

Figure 5:
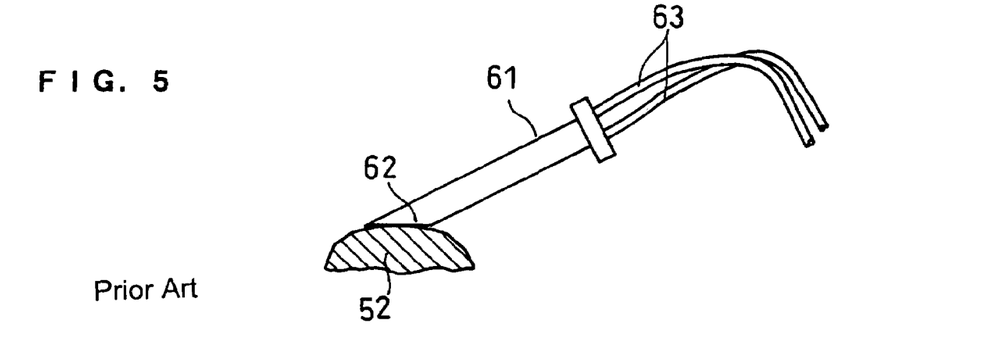
FIG. 5 is another view illustrating the operation of a conventional biological attribute measuring device.

According to "Fiber Optics User's Manual", of Spectra-Tech, Version 2.0 (pages 2 and 9), an optical fiber ATR probe 61 as shown in FIG. 5 is disclosed as a form of a prism. When an ATR probe 62 is made contact with a lip 52, light propagated from the light source side (not shown) of an optical fiber 63 through the ATR prove 62 enters the lip 52 and is reflected, and then the reflected light is propagated to the light reception side (not shown) of the optical fiber 63. However, conventional measuring devices as described above have the following problems.

For example, a penetration depth is calculated by a known formula under the conditions that light of 10 microns in wavelength and an ATR prism made of a ZnSe crystal (refractive index: about 2.0) are used, an incident angle is set at 45° and water is used as a surrounding medium (refractive index: about 1.24). The penetration depth obtained herein is 4.7 microns. If the refractive index of the surrounding medium is varied, the penetration depth is also varied. In any event, however, the penetration depth is a few microns at the highest.

In other words, conventional measuring devices allow measurement of information about the surface and its vicinity of the living body. However, if a disturbance layer such as saliva exists between the ATR prism and the subject, light may not reach the living body or the depth of light entering the living body may vary, which makes the obtained signal unstable.

Further, if water and air exist in part of a sensing part of the ATR prism, or water exists on the whole surface of the sensing part of the ATR prism, a spectrum obtained is varied in shape. An intervenient air layer is also a cause of the variation in spectrum.

Therefore, when the ATR prism is sandwiched between the lips to be pressed by them as in the above-described prior art technique, the degree of contact varies depending on a force closing the lips. Accordingly, the contact between the ATR prism surface and the lips becomes unstable and the thickness of the saliva layer becomes difficult to control. Further, due to the influence of an intervenient air layer or the like, measurement data is apt to vary. Even if the saliva layer is wiped off, the contact is insufficient because a oral mucosa has a surface with fine irregularity, and therefore the air layer may exist if the contact is not achieved.

The larger the contact region of the ATR prism is, the more difficult it becomes to realize completely uniform contact. Then, an optical fiber ATR probe 61 as shown in FIG. 5 is considered as the one having a small contact region. The linear ATR probe has a corner 62 which is edged or slightly rounded. Accordingly, when pressed strongly against the lip for contact, the corner may cause pain in the lip contacting thereto. This may weaken the pressing force, resulting in unstable contact.

According to BME, Vol.5, No. 8 (Japanese Society for Medical and Biological Engineering, 1991), there has been proposed a method of measuring a blood glucose level and an ethanol concentration in blood by bringing an ATR element made of an ZnSe optical crystal or the like into contact with a labial mucosa, introducing a laser beam of 9 to 11 microns in wavelength into the ATR element to cause multiple reflection of the laser beam in the inside of the ATR element, and analyzing absorbed light, scattered light or reflected light.

This method allows real-time and noninvasive measurement of a concentration of a specific component such as glucose, ethanol or cholesterol. Also in this method, evanescent wave (penetrating wave) is applied to the quantitative analysis.

Light traveling in the ATR element slightly gets into the lips and is affected by components contained in a body fluid existing there. For example, glucose shows a light absorption peak at a light wave number of 1080 $cm^{-1}$.

Therefore, if light of this wave number is applied to a living body, the amount of light absorption varies depending on variations in glucose concentration in the living body. Thus, variations in light absorption due to variations in concentration of body fluid components are detected by measuring light returned from the living body, thereby obtaining a concentration of each component.

In general, however, the ATR measurement device is used for surface analysis of a substance and an incident angle of 45° is adopted in most cases. Therefore, the depth to which the evanescent wave enters is almost at the same level as the wavelength, i.e., the light passes only a small distance in the living body.

Accordingly, an optical path of light passing through the body fluid is extremely short and hence the amount of light absorbed in the body fluid is very small. Therefore, a sufficiently large signal strength cannot be obtained by a single total reflection.

For this reason, there has been attempted to increase the signal strength by repeating the total reflection. However, in order to reflect the light many times, the element itself needs to be upsized, which is problematic because the cost of the optical element increases. Further, as a result of the upsizing of the element, the region to be measured becomes large, and hence it becomes relatively difficult to obtain a signal from a region which is truly required to be measured.

In view of the foregoing points, a first object of the present invention is to provide a biological attribute measuring method and a biological attribute measuring device that allow highly accurate measurement by easily bringing a prism comprising a contact device into contact with a measuring region.

Further, a second object of the present invention is to provide a biological attribute measuring method and a biological attribute measuring device for measuring a concentration of a specific component by obtaining a large measurement signal with a small optical element.

DISCLOSURE OF INVENTION

The biological attribute measuring method according to the present invention comprises the steps of: (1) bringing a contact device having a portion, at least part of which is a curved surface, for abutting against a measuring region of a measuring object into contact with the measuring region; (2) applying first light to the measuring region from the contact device; (3) detecting at least one kind of second light selected from the group consisting of transmitted light, reflected light, scattered light and transmitted from the measuring region; and (4) measuring a specific component noninvasively in the measuring region based on the detection result to obtain biological attribute.

As to the biological attribute measuring method, the first light preferably includes evanescent wave.

Further, it is preferred that the measuring object is a living body and the biological attribute is a glucose concentration.

Still further, the first light preferably has a wavelength of 8.4 to 10 μm.

The biological attribute measuring device according to the present invention comprises: a contact device having a portion, at least part of which is a curved surface, for abutting against a measuring region of a measuring object to apply first light to the measuring region; a light detecting means for detecting at least one kind of second light selected from the group consisting of transmitted light, reflected light, scattered light and transmitted/reflected light from the measuring region; and a measuring means for measuring a specific component noninvasively in the measuring region based on the detection result to obtain biological attribute.

As to the biological attribute measuring device, it is preferred that the portion of the contact device for abutting against the measuring region is entirely a curved surface.

It is preferred that the portion of the contact device for abutting against the measuring region is a flat surface and a corner thereof is rounded.

The biological attribute measuring device preferably has a light shielding means at the corner.

The measuring region is preferably a labial mucosa of a lip of a living body.

The contact device is preferably made of germanium or silicon.

The portion of the contact device for abutting against the measuring region preferably has an area of 2 cm$^2$ or smaller.

The biological attribute measuring device preferably comprises a light flux blocking means for controlling an incident angle of the first light.

The light flux blocking means is preferably a notch.

The notch preferably includes a first notch provided between a part of the contact device from which light is input and a part of the contact device abutting against the measuring region and a second notch provided between a part of the contact device from which light is output and the part of the contact device abutting against the measuring region.

The light flux blocking means is preferably a light shielding film.

The light flux blocking means preferably includes a light absorber.

The light absorber is preferably oxide.

The oxide is preferably silicon dioxide.

BEST MODE FOR CARRYING OUT THE INVENTION

The present invention relates to a biological attribute measuring method in which first light is applied from a contact device for detecting information which abuts against a measuring region and second light, i.e., returned light from the measuring region such as transmitted light, reflected light, scattered light or transmitted/reflected light, is detected to measure a specific component in the measuring region in a noninvasive manner. The method is characterized in that at least part of the contact device to be in contact with a labial mucosa of a lip of a living body, which is a measuring region, is configured as a curved surface.

More specifically, the biological attribute measuring method according to the present invention comprises the steps of:

(1) bringing a contact device having a portion, at least part of which is a curved surface, for abutting against a measuring region of a measuring object into contact with the measuring region;

(2) applying first light to the measuring region from the contact device;

(3) detecting at least one kind of second light selected from the group consisting of transmitted light, reflected light, scattered light and transmitted/reflected light from the measuring region; and (4) measuring a specific component in the measuring region based on the detection result in a noninvasive manner to obtain biological attribute.

Further, the present invention relates to a biological attribute measuring device used in the biological attribute measuring method in which first light is applied from a contact device for detecting information which abuts against a measuring region and second light, i.e., returned light from the measuring region such as transmitted light, reflected light, scattered light or transmitted/reflected light, is detected to measure a specific component in the measuring region in a noninvasive manner. The device is characterized in that at least part of the contact device to be in contact with a labial mucosa of a lip of a living body, which is a measuring region, is configured as a curved surface.

In other words, the biological attribute measuring device according to the present invention comprises:

a contact device having a portion, at least part of which is a curved surface, for abutting against a measuring region of a measuring object to apply first light to the measuring region;

a light detecting means for detecting at least one kind of second light selected from the group consisting of transmitted light, reflected light, scattered light and transmitted/reflected light from the measuring region; and a measuring means for measuring a specific component noninvasively in the measuring region based on the detection result to obtain biological attribute.

As to the biological attribute measuring device, a surface of the contact device to be brought into contact with a labial mucosa of a lip of a living body, which is the measuring region, may entirely be curved. Alternatively, part of the contact device to be brought into contact with a labial mucosa of a lip of a living body, which is the measuring region, may be made into a flat surface and a corner thereof may be rounded. Further, the corner of the contact device may have a light shielding property.

As to the biological attribute measuring method, on conditions that a refractive index of the measuring object is represented by $n_c$, a refractive index of the portion of the contact device contacting the measuring object by $n_f$ and an incident angle of the first light with respect to a contacting surface of the contact device by θ, it is preferred to adjust the incident angle θ so that a penetration depth z (a depth to which the first light seeps from the contact device into the measuring object) obtained by the formula (1):

$$\frac{z}{\lambda} = \frac{1}{2\pi\sqrt{nf^2\sin^2\theta - nc^2}} \quad (1)$$

is not less than 10 μm.

When the measuring object is a living body and the specific component is glucose, light having a wavelength of 8.4 to 10 μm (1000 $cm^{-1}$ to 1180 $cm^{-1}$), which is an absorption wavelength of glucose, is preferably used as light incident on the contact part.

Further, in order to detect mainly light propagated through the measuring object with stability without detecting unnecessary light applied to other surfaces of the ATR prism, it is preferred in the step (3) to measure the intensity of the second light propagated through the measuring object and then returned to the contact device without re-applying the second light to the measuring object.

The contact device according to the present invention includes a contact part for closely abutting against the measuring object, a light input part for applying light to the contact device and a light output part for emitting the second light which seeped from the contact part to propagate through the measuring object and then returned to the contact part.

As described above, in order to emit the second light which has propagated through the measuring object and then returned to the contact part from the light output part without applying the second light again to the measuring object from the contact part, the shape of the contact device is adjusted as appropriate to control the optical path.

From the viewpoint of controlling the optical path, the biological attribute measuring device according to the present invention is preferably provided with a light flux blocking means for limiting the light incident angle with respect to the contact surface of the contact part within a predetermined range. As the light flux blocking means, a notch formed in the contact device or a light shielding film may be used. With the light flux blocking means integrated with the contact device, displacement of the light flux blocking means and the optical path due to an influence of vibration or heat is prevented, which is advantageous.

Further, in order to prevent light reflected by the light flux blocking means from entering the light detecting means to cause bad influence, the light flux blocking means preferably includes a light absorber. Thereby, the light reflection is eliminated.

Hereinafter, embodiments of the present invention will be described with reference to FIGS. 1 to 6. However, the present invention is not limited thereto.

Embodiment 1

Figure 1:
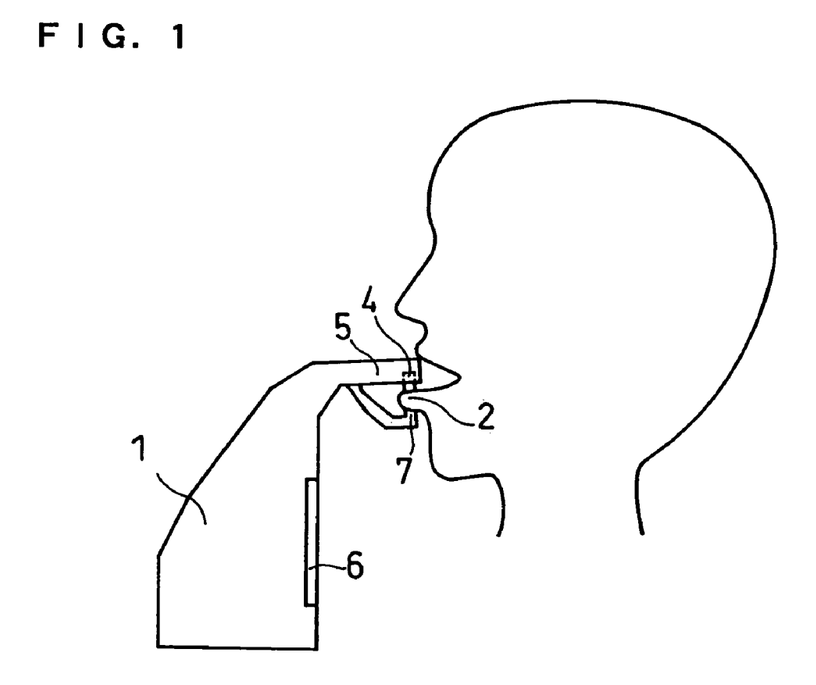
FIG. 1 is a side view schematically illustrating a biological attribute measuring device according to Embodiment 1 of the present invention which is in use.
Figure 2:
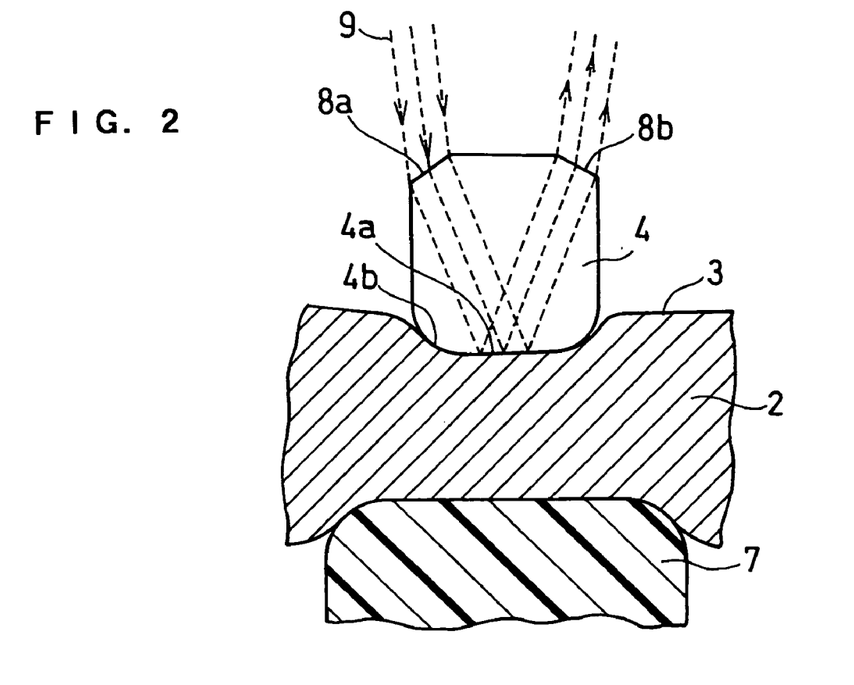
FIG. 2 is a partial sectional view illustrating the biological attribute measuring device of FIG. 1 in detail.
Figure 3:
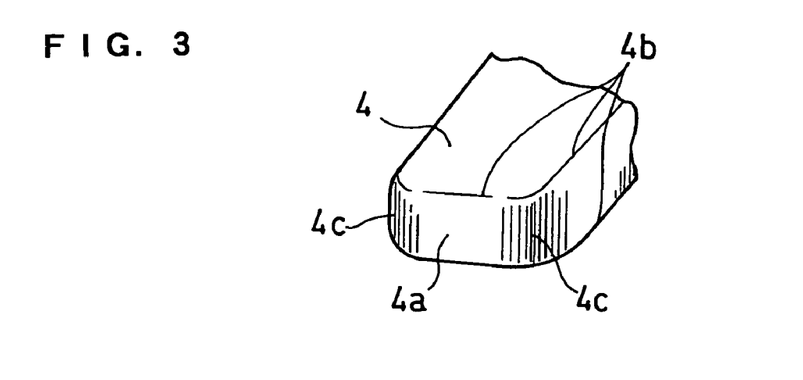
FIG. 3 is an oblique view of a contact device of the biological attribute measuring device of FIG. 1.

FIG. 1 is a side view schematically illustrating a biological attribute measuring device 1 according to Embodiment 1 of the present invention which is in use. FIG. 2 is a partial sectional view illustrating the biological attribute measuring device 1 of FIG. 1. FIG. 3 is an oblique view of a sensing part, i.e., a contact device of the biological attribute measuring device of FIG. 1. In FIGS. 1 to 3, components having the same function are indicated by the same reference numerals and repetitive explanations are omitted.

As shown in FIG. 1, the biological attribute measuring device 1 of the present invention is of a desk-top type, for example, and includes a prism 4 which serves as a contact device abutting against a labial mucosa 3 of a lower lip 2 as shown in FIG. 2 and an arm 5 having the prism 4 on the tip thereof. Though not shown, the device incorporates a light source, a light guiding means for introducing light from the light source into the prism 4 to propagate first light once seeped into the labial mucosa 3, which is the abutting measuring region (sample), into the prism 4, and a detector (light detecting means) for receiving second light such as reflected light.

In the prism 4, a sensing part 4a which abuts against the labial mucosa 3 for sensing is preferably downsized to have a sensing area of not more than a half area of the lip 2 and is projected from a face of the arm 5. The desk-top type biological attribute measuring device 1 preferably includes a lip support 7 which is movable and fixable for supporting the lip from the bottom. Further, the biological attribute measuring device 1 incorporates therein a measuring part including, though not shown, an arithmetic circuit for processing the result of light detection. Data from the measuring part can be shown in a display 6 provided at a front face or a rear face.

In the biological attribute measuring device 1 according to the present invention, a surface of the prism 4 abutting against the labial mucosa 3 includes curved surfaces 4b and 4c other than the sensing part 4a which is flat. Another surface includes a light introducing surface 8a for introducing light 9 from the light source to the labial mucosa 3 and a light emitting surface 8b for introducing the light 9 seeped from the labial mucosa 3 into the light guiding means. The portions from which the light 9 is introduced or emitted may have other shapes than the above.

The lip support 7 has an area larger than that of the prism 4 and the corners thereof abutting against the lip are rounded.

Hereinafter, explanation is given of the operation of the desk-top type biological attribute measuring device 1 configured as described above according to this embodiment.

When the lip 2 is made contact with the prism 4 and the lip support 7 is shifted to press the bottom of the lip 2, the labial mucosa 3 is brought into contact with the sensing part 4a. At this time, since the prism 4 has corners which are not edged but rounded, pain is not caused even if the prism is strongly pressed against the labial mucosa 3. Further, the labial mucosa 3 fits the prism 4 by itself with the shape of the prism 4, and therefore contact can surely be achieved.

In addition, since the area of the prism 4 abutting against the labial mucosa 3 is smaller than the lip surface, a force applied to the surface to be pressed is concentrated and the degree of the contact increases. The lip support 7 is equal or larger than the prism 4 in area, and hence the labial mucosa 3 abutting against the sensing part 4a can surely be pressed onto the entire surface of the sensing part 4a. Fine irregularity on the lip 2 is eliminated by being pressed from the bottom, which inhibits the intervention of an air layer.

Moreover, since the portion which is pressed to be in contact is small in area and is rounded, saliva on the labial mucosa 3 is easily dispersed from the center of the sensing part 4a to surrounding regions which are not pressed between the sensing part 4a and the lip support 7. Therefore, variations in the saliva layer on the labial mucosa 3 are reduced to a great extent.

According to this embodiment, the lip support 7 is configured to be movable. However, the prism 4 may be shifted to press the lip. In short, it is sufficient that the labial mucosa 3 and the sensing part 4a are brought into contact by shifting the lip support 7 or the prism 4 until the lip support 7 and the sensing part 4 of the prism 4 bite into the lip.

When an operation switch of the biological attribute measuring device 1 is turned ON, first light from the built-in light source enters the labial mucosa 3 through the light guiding means and the prism 4 as described above. Then, returned second light is received by the detector and blood glucose level data obtained by the arithmetic circuit is shown in the display 6. It is advantageous that the data is stored in a memory circuit, which is not shown, so that past data can be retrieved at any time at one's will.

With a simple structure in which the lip support 7 is shifted and then fixed, the contact to the labial mucosa 3 can easily and reliably be achieved with a single motion. According to this embodiment, the biological attribute measuring device is of desk-top type. However, it may be of a portable type.

If the curved surfaces 4b and 4c other than the sensing part 4a are provided with a light shielding film, unwanted light other than light required for the sensing is inhibited. It is sufficient that the sensing part 4a is configured such that the light to be sensed is propagated into the detector. If the sensing part 4a is not flat but slightly curved, the contact of the sensing part can be achieved more readily and the saliva is dispersed easily. Therefore, variations in the saliva layer on the labial mucosa 3 are reduced to a greater extent.

Embodiment 2

Figure 6:
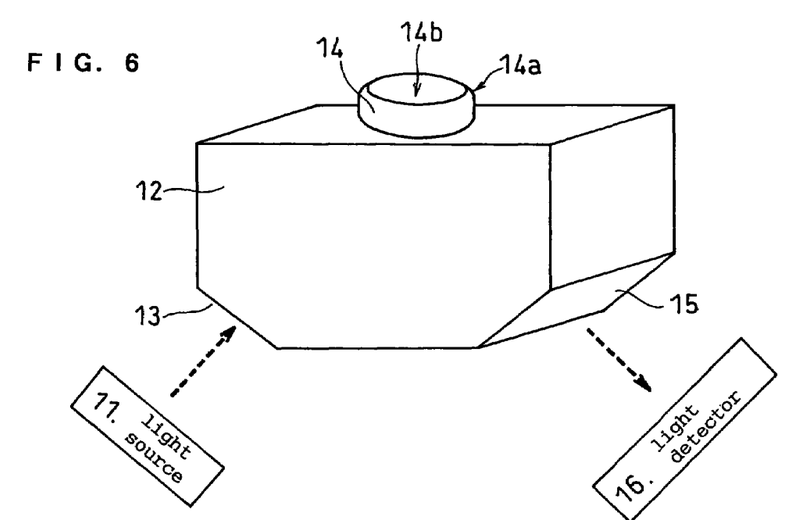
FIG. 6 is a schematic sectional view illustrating a contact device of a biological attribute measuring device according to Embodiment 2 of the present invention.
Figure 7:
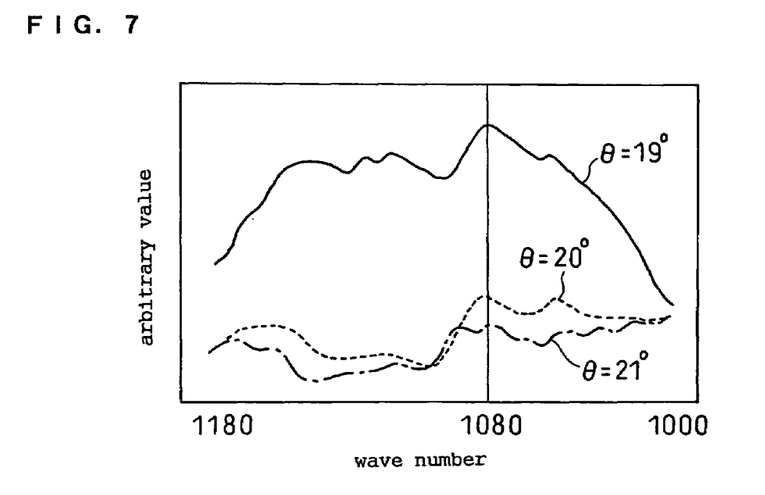
FIG. 7 is a graph showing spectra measured by using the contact device of the biological attribute measuring device according to Embodiment 2 of the present invention.

A biological attribute measuring device according to Embodiment 2 of the present invention is explained with reference to FIGS. 6 to 8. FIG. 6 is an oblique view illustrating a contact device used in a biological attribute measuring device according to Embodiment 2 of the present invention.

In this embodiment, explanation is given of an example in which the contact device is brought into contact with a living body, which is a measuring object, to measure a concentration of a specific component, i.e., glucose.

As a light source 11, for example, a light source which generates mid-infrared light is preferably used. For example, use of a light source made of tungsten or SiC is preferable. In particular, for measuring a concentration of a substance having an adsorption wavelength of 1000 $cm^{-1}$ to 1180 $cm^{-1}$, or about 1080 $cm^{-1}$ to 1033 $cm^{-1}$, such as glucose, these light sources are preferably used. These light sources may be used in other embodiments of the present invention.

It is preferred that a material for a contact device 12 allows mid-infrared light to pass through and has chemical stability and excellent mechanical strength. For example, germanium or silicon is used. This material may be used in other embodiments of the present invention.

If silicon is used as the material for the contact device 12, for example, a monocrystalline silicon substrate which is transparent to light of 1.1 to 10 µm in wavelength is preferably used. In particular, a monocrystalline silicon substrate containing less impurities such as boron and phosphorus and having resistivity not less than 100 Ωcm is preferable. It is further preferable that the resistivity is 1500 Ωcm or more. Silicon having high resistivity shows high transmittance to infrared wavelength of about 9 to 10 µm and is preferably used for measuring a substance having an absorption wavelength within this wavelength range, such as glucose.

A light input part 13 is preferably provided with an antireflection film on its surface. As a material for the antireflection film, for example, diamond-like carbon (DLC) or ZnSe is preferably used. The antireflection film preferably has a thickness of about 1.1 to 1.3 µm, more preferably about 1.2 µm.

A contact part 14 abutting in contact against a measuring region of a living body which is a measuring object includes a curved surface 14a in the same manner as the prism 4 serving as the contact device in Embodiment 1 described above.

An area of the contact part 14 closely contacting the measuring region is preferably 2 $cm^2$ or smaller. With the area kept 2 $cm^2$ or smaller, the contact part 14 can bite deeper into the measuring region and the contact between the contact part 14 and the measuring region is enhanced, thereby stable measurement is allowed.

The shape of the contact part 14 is not particularly limited as long as the above-described curved surface is provided. However, if the measuring object is a living body, a substantially round-shaped contact part is preferable because it causes less pain during measurement. For example, the contact part 14 may be provided with a beveled portion or a rounded portion on the periphery thereof to further alleviate pain.

A light output part 15 is preferably provided with an antireflection film as is the case with the light input part 13.

Thus, in the contact device 12 according to Embodiment 2, the light input part 13, the contact part 14 and the light output part 15 are integrated and light returned through the contact part 14 is directly emitted as second light from the light output part 15 without being applied to the contact part 14 again. For example, as compared with the case where returned light is reflected on a different surface and applied to the contact part again, this structure is advantageous in that influence caused by pollution on the different surface is eliminated and the measurement is carried out with stability.

Next, explanation is given of an incident angle θ of light incident on a contact surface 14b of the contact part 14. The incident angle θ is obtained by the foregoing formula (1), provided that z represents the penetration depth (μm), λ is a wavelength (μm) of light incident on the contact part 14, $n_f$ is a refractive index of the contact part 14, θ is an incident angle of light incident on the contact surface of the contact part and $n_c$ is a refractive index of the measuring object.

For example, in the case where the measuring object is a living body having a refractive index nc=1.3, the contact part is made of germanium having a refractive index nf=4, the penetration depth z is 10 μm and an absorption wavelength of glucose is about 9.6 μm, an incident angle θ of about 21° is obtained from the above-described formula (1).

With the incident angle set at 21°, 20° or 19°, the contact device 12 according to Embodiment 2 was made contact with the labial mucosa to measure spectra. FIG. 7 shows the measurement results. As seen in FIG. 7, when the incident angle was 21°, an absorption peak was observed in the absorption wavelength of glucose. When the incident angle was 20°, an absorption peak also appeared at 1080 cm$^{-1}$ and the S/N was improved as compared with the case where the incident angle was 21°. When the incident angle was 19°, it was observed that absorbance was dramatically improved as compared with the case where the incident angle was 20°. This is because of an increase in absorbance of the penetration depth z increased to about 78 μm. Thus, with the incident angle set at about 21°, i.e., the penetration depth z set at 10 μm or more, excellent measurement of the glucose concentration was achieved.

Embodiment 3

A biological attribute measuring device according to Embodiment 3 of the present invention is described with reference to FIG. 8. FIG. 8 is a schematic sectional view illustrating a contact device of the biological attribute measuring device according to Embodiment 3 of the present invention.

Light 32 emitted from a light source 31 is radiated in all directions. It is preferred to gather the radiated lights as much as possible with a curved mirror or a lens (not shown) to introduce them as a parallel ray (second light) into a light input part 40 of a contact device 33.

However, when the light source 31 is not a point light source, it is difficult to make the light 32 into a complete parallel ray and hence an incident angle θ of light incident on a contact part 34 is not fixed. Therefore, light having an incident angle $\theta_1$ as shown in FIG. 8 reaches a light detector 36 through a light output part 35 and may have a great influence on measurement values, because a change in incident angle of light incident on a contact surface 34b of the contact part 34 varies a path of light propagating into the living body.

Therefore, it is preferred to limit the incident angle θ within a specific range.

In order to limit the range of the incident angle θ, part of the contact device is cut away to provide a first notch 37 and a second notch 38. That is, with the first and second notches 37 and 38, the shape of the contact device 33 is controlled to prevent light having an incident angle θ beyond the predetermined range from reaching the contact surface 34b of the contact part 34. As a result of this, unwanted light having an incident angle beyond the specific range is blocked, thereby inhibiting the unwanted light from reaching the light detector 36.

Figure 8:
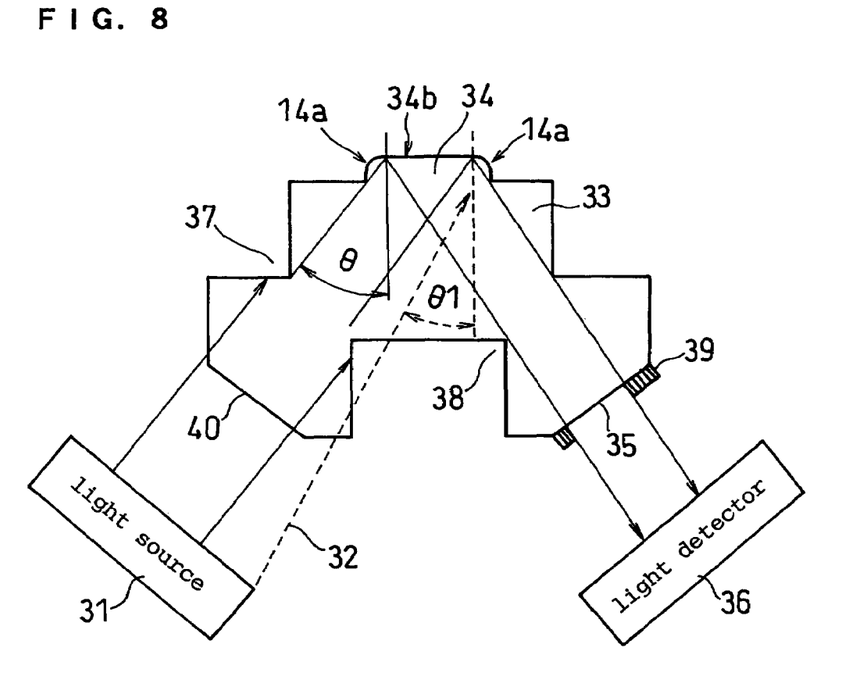
FIG. 8 is a schematic sectional view of a contact device of a biological attribute measuring device according to Embodiment 3 of the present invention.

As shown in FIG. 8, by providing two or more notches, the second light reaching the light detector 36 is further limited and a greater amount of a light component incident on the contact surface 34b of the contact part 34 at the specific incident angle can be detected. The first notch 37 and/or the second notch 38 may be provided with a light absorber.

It is preferred to provide a light shielding film 39 on a light input part 40 or a light output part 35 so that unwanted second light is not incident on the light detector 36. As materials for the light shielding film 39, those capable of blocking light are preferable. Examples thereof include, for example, aluminum, silver, gold, tungsten and tungsten silicide and the like. If a light absorber is used as the light shielding film 39, it preferably reduces the amount of light which is reflected on the light shielding film 39, repetitively reflected in the inside of the contact device 33 and then enters the light detector 36 again.

As a material for the light absorber, are preferable titanium dioxide, silicon dioxide, tantalum oxide and zirconium oxide because they particularly absorb a great amount of light having an absorption wavelength of glucose. Among them, silicon dioxide is particularly preferable because of its high light absorption ability and low cost.

The light detector 36 is not particularly limited, but for example, a pyroelectric sensor or an MCT detector may be used.

Though not particularly shown, if a spectroscopic means is placed between the light source 31 and the contact device 33, for example, wavelength spectral characteristics of a specific component are measured to obtain absorption characteristics at various wavelengths. In particular, an FT-IR method, i.e., spectroscopy using an interferometer, is preferable because it allows highly sensitive measurement.

INDUSTRIAL APPLICABILITY

As described above, according to a biological attribute measuring device of the present invention, a stable signal is obtained by making a lip and a prism in contact in a simple, reliable and safety manner. Thereby, highly sensitive measurement is allowed without variations in measurement data.

Further, according to a biological attribute measuring device of the present invention, a large measurement signal is obtained with a small optical element.

The invention claimed is:

1. A biological attribute measuring device comprising:
   a contact device having a portion, at least part of which is a curved surface, for abutting against a measuring region of a measuring object to apply a first light to said measuring region;

a light detecting means for detecting at least one kind of a second light selected from the group consisting of transmitted light, reflected light, scattered light and transmitted/reflected light from said measuring region;

a measuring means for measuring a specific component in said measuring region based on the detection result to obtain biological attribute; and a light flux blocking means for controlling an incident angle of said first light.

2. The device in accordance with claim 1, wherein said light flux blocking means is a notch.

3. The device in accordance with claim 2, wherein said notch includes a first notch provided between a part of said contact device from which light is input and a part of said contact device abutting against said measuring region and a second notch provided between a part of said contact device from which light is output and the part of said contact device abutting against said measuring region.

4. The device in accordance with claim 2, wherein said light flux blocking means is a light shielding film.

5. The device in accordance with claim 2, wherein said light flux blocking means includes a light absorber.

6. The device in accordance with claim 5, wherein said light absorber is oxide.

7. The device in accordance with claim 6, wherein said oxide is silicon dioxide.

* * * * *

UNITED STATES PATENT AND TRADEMARK OFFICE
CERTIFICATE OF CORRECTION

| | | |
|---|---|---|
| PATENT NO. | : 7,262,836 B2 | Page 1 of 1 |
| APPLICATION NO. | : 10/489175 | |
| DATED | : August 28, 2007 | |
| INVENTOR(S) | : Shinji Uchida et al. | |

It is certified that error appears in the above-identified patent and that said Letters Patent is hereby corrected as shown below:

On the title page
Item (56) References cited, OTHER PUBLICATIONS, add -- "Fiber Optics User's Manual" Spectra-tech, Version 1.0PN/700-0043, pp. 16 --

Signed and Sealed this

Seventh Day of April, 2009

JOHN DOLL
*Acting Director of the United States Patent and Trademark Office*